United States Patent
Herman

(10) Patent No.: US 11,098,320 B2
(45) Date of Patent: Aug. 24, 2021

(54) ENGINEERING HIGH-PROTEIN-CONTENT SOYBEANS

(71) Applicant: ARIZONA BOARD OF REGENTS ON BEHALF OF THE UNIVERSITY OF ARIZONA, Tucson, AZ (US)

(72) Inventor: Eliot M. Herman, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 16/483,172

(22) PCT Filed: Feb. 2, 2018

(86) PCT No.: PCT/US2018/016620
§ 371 (c)(1),
(2) Date: Aug. 2, 2019

(87) PCT Pub. No.: WO2018/144843
PCT Pub. Date: Aug. 9, 2018

(65) Prior Publication Data
US 2019/0352658 A1    Nov. 21, 2019

Related U.S. Application Data

(60) Provisional application No. 62/454,606, filed on Feb. 3, 2017.

(51) Int. Cl.
*C12N 15/82* (2006.01)
*C07K 14/415* (2006.01)

(52) U.S. Cl.
CPC ..... *C12N 15/8251* (2013.01); *C12N 15/8216* (2013.01); *C12N 15/8293* (2013.01); *C07K 14/415* (2013.01)

(58) Field of Classification Search
None
See application file for complete search history.

(56) References Cited

U.S. PATENT DOCUMENTS

| 6,392,121 B1 | 5/2002 | Mason et al. |
| 7,723,570 B2 | 5/2010 | Piller et al. |
| 2003/0041350 A1 | 2/2003 | Kinney et al. |
| 2003/0228612 A1 | 12/2003 | Kenward et al. |
| 2005/0193443 A1* | 9/2005 | Dale Rock ......... C12N 15/8273 800/278 |
| 2006/0135758 A1* | 6/2006 | Wu .................. C07H 21/04 536/24.3 |

FOREIGN PATENT DOCUMENTS

| WO | WO 1998021348 | 5/1998 |
| WO | WO2007095304 A2 | 8/2007 |
| WO | WO2014097733 A1 | 6/2014 |

OTHER PUBLICATIONS

Smith et al. (Nature Biotechnology, 15:1222-1223, 1997).*
Bork et al. (TIG, 12:425-427, 1996).*
Doerks et al., (TIG, 14:248-250, 1998).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
Li et al. (PLoS ONE 10(2):e0118056.doi:10.1371/journal.pone.0118056; 2015).*
Liu et al. (Plant Science, 275, 49-59, 2018).*
Sun et al. (The Plant Journal, 40:870-881; 2004).*
Liu et al. (Journal of Plant Physiol., 166:531-542, 2009).*
Nunes et al. (Planta 224:125-132; 2006).*
Rivin et al. (Plant Physiol., 95:358-365, 1991).*
Keddie et al. (Plant Molecular Biology, 19:443-453, 1992).*
Kim et al. (Mol. Cells, 16:393-399, 1996).*
Zhang et al. (Genes and Development, 19:1532-1543; Published 2005).*
Genbank (NCBI, Sequence Accession No. XM_003550182; Published Nov. 8, 2011).*
Wang et al. (Plant Cell Rep. 27:1177-1184, Published 2008).*
He et al. Transgenic Soybean Production of Bioactive Human Epidermal Growth Factor (EGF). PLOS One | DOI:10.1371/journal.pone.0157034 Jun. 17, 2016.
Rivin et al., Abscisic Acid and the Developmental Regulation of Embryo Storage Proteins in Maize, Plant Physiol., 1991, 95, 358-365; abstract, p. 362, col. 1, para 1, p. 363, col. 1, para 3.
Kinney et al., Cosuppression of the α subunits of β conglycinin in transgenic soybean seeds induces the formation of endoplasmic reticulum-derived protein bodies, Plant Cell, 2001, 13:1165-1178.
Schmidt et al., Silencing of soybean seed storage proteins results in a rebalanced protein composition preserving seed protein content without major collateral changes in the metabolome and transcriptome, Plant Physiology, 2011, 156: 330-345.
Herman, Soybean Seed Proteome Rebalancing, Front. Plant Sci., 2014, 5:437. doi:10.3389/fpls.2014.00437.
Schmidt et al., Transgenic soya bean seeds accumulating β-carotene exhibit the collateral enhancements of oleate and protein content traits, Plant Biotechnol. J., 2015, 13: 590-600. doi: 10.IIII/pbi.12286.
Rowley et al., The upstream domain of soybean oleosin genes contains regulatory elements similar to those of legume storage proteins, Biochim. Biophys. Acta., 1997, 1345: 1-4.

(Continued)

Primary Examiner — Vinod Kumar
(74) Attorney, Agent, or Firm — Nguyen Tarbet LLC

(57) ABSTRACT

The invention relates to high-protein-content soybeans and methods of producing high-protein-content soybeans. The methods can relate to proteome rebalancing and regulating the abscisic acid (ABA) pathway. The methods can relate to modulating transcription factors such as AiP2. AiP2 modification can increase soybean protein content and indicates the strategic path to alter seed protein is contained within the mechanisms of abscisic acid control of seed development.

4 Claims, 5 Drawing Sheets
Specification includes a Sequence Listing.

(56) References Cited

OTHER PUBLICATIONS

Schmidt et al., The potential of engineering functional-feed soybeans for sustainable aquaculture feed, Front Plant Sci., 2016, 7: 440. Doi:10.3389/fpls.2016.00440.

Schmidt et al., Proteome rebalancing in soybean seeds can be exploited to enhance foreign protein accumulation, Plant Biotech J., 2008, 6: 832-842.

* cited by examiner

ENGINEERING HIGH-PROTEIN-CONTENT SOYBEANS

CROSS-REFERENCE TO RELATED APPLICATION

This application claims the benefit of U.S. Provisional Application No. 62/454,606, filed Feb. 3, 2017, entitled *Engineering High-Protein-Content Soybeans*. The entire contents of the foregoing are hereby incorporated by reference herein.

BACKGROUND

Soybeans are legumes that are high in protein and oil. Soybeans are used to provide protein for animal feed and are used in renewable primary products. In addition, they provide the raw materials for many food products including: soy protein products, soybean oil, soy flour, plant oils and fats, tocopherol (vitamin E), and lecithin and other emulsifiers.

According to the US Department of Agriculture, 94% of soybeans grown in the U.S. in 2012 were genetically modified. Genetically modified soybeans have improved the productivity of farmers due to their increased resistance to weeds. Most of the currently available genetically engineered soybeans are designed for weed control and to tolerate the herbicide glyphosate. There are no genetically engineered soybeans in the market that are able to provide other benefits, such as modified composition to increased protein content.

Soybeans are the primary global source of plant-source protein. About 70% of the global protein input for animal feed is obtained from soybean. The soybean industry has a strategic goal of increasing seed protein content with additional goals to also increase sulfur amino acid content while preserving maximum oil content. From the perspective of farmer/producers each increase of 1% protein in the seed increases crop value of 10-12 dollars per acre. Industry has a general goal of increasing protein by 3% or more and an ideal composition of 62% protein and oil. Soybean seed protein content is regulated by genotype and can be bred as a trait. Protein composition—termed proteome rebalancing, is in contrast far more plastic, and can be significantly altered by changing the protein types in the seed while conserving genotype-specific protein content.

SUMMARY

Embodiments of the invention relate to a method of increasing protein production in a plant including: expressing a polynucleotide that functions to modulate abscisic acid (ABA)-regulated gene expression in a plant, where expressing the isolated polynucleotide produces a high-protein plant. In some embodiments, the plant can be a soybean plant. In some embodiments, the high-protein can be accumulated primarily in seeds of the plant.

In some embodiments, the invention relates to a plant having altered ABA-regulated gene expression, wherein the alteration can result in an elevated level of protein expression and accumulation. In some embodiments, the plant can be a soybean plant and the elevated level of protein accumulation can include a seed having elevated protein content as compared with a control plant having normal ABA-regulated gene expression.

Some embodiments of the invention relate to a polynucleotide including an active sequence capable of causing altered ABA-regulated gene expression in a plant and further including at least one other sequence capable of enabling or enhancing expression of the active sequence. In some embodiments, the active sequence comprises SEQ ID NOs 1 or 2. In some embodiments, the polynucleotide comprises an expression cassette including the active sequence, wherein the active sequence is linked to a promoter. In some embodiments, the promoter is oleosin.

Some embodiments of the invention relates to a vector comprising the polynucleotide.

Some embodiments relate to a soybean plant comprising the polynucleotide sequence.

Some embodiments relate to a method of producing a high-protein soybean comprising: expressing the isolated polynucleotide in a soybean, where the expressing the isolated polynucleotide produces a high-protein soybean.

In some embodiments, the soybean is from a conventional breeding line.

DETAILED DESCRIPTION

Figure 1:
FIG. 1 depicts a diagrammatic representation of the gene construct used to alter AiP2 expression in soybean. This construct comprises soybean DNA including the regulatory upstream and downstream elements from the soybean oleosin gene and the AiP2 elements comprising either the 313 amino acid open reading frame for over-expression with a FLAG tag or a RNAi sequence with a hairpin sequence for suppression
Figure 2:
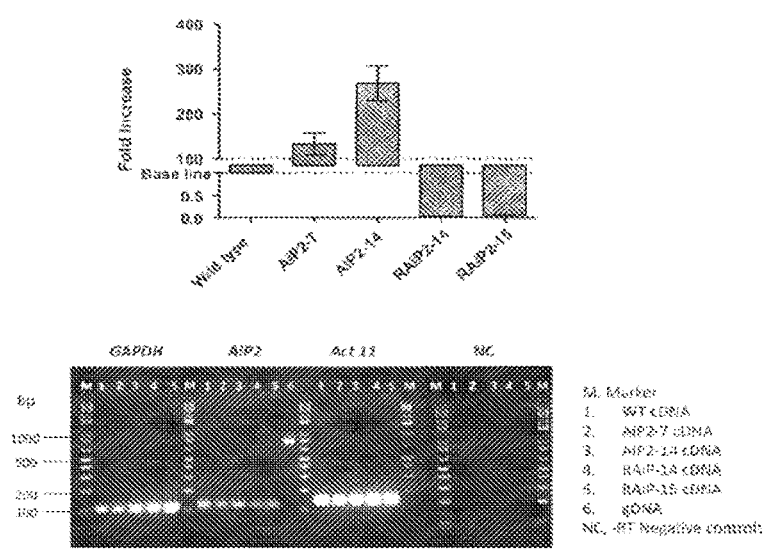
FIG. 2 depicts a Real-time PCR quantitative transcript analysis of AiP2 gene expression in control Jack compared to AiP2 over-expression and silenced seeds. The oleosin promoter regulation resulted in 130-250 fold increase in transcript abundance in the over-expression lines compared to significant silencing of the AiP2 transcripts in the RNAi silenced lines compared to the control baseline. Gel analysis of the amplified products compared to the control showed specificity of the AiP2 primers used and in control GAPDH and act11 genes. The modification of the AIP2 gene expression altered soybean seed composition changing protein, oil, and S-amino acid content.

The invention relates to high-protein-content soybeans and methods of producing high-protein-content soybeans.

The invention can relate to proteome rebalancing and regulating the plant hormone abscisic acid (ABA) pathway.

The invention relates to the underlying biology of proteome rebalancing to alter seed protein content. Proteome rebalancing refers to an intrinsic process seeds in which a shortfall in a major protein induced by either mutation or engineering results in other proteins accumulated with increased abundance that quantitatively compensates for the absent protein. Proteome rebalancing is central to maintaining a standardized protein content trait that can be bred as a trait. Standardized output traits are key to agriculture allowing for predictable yields at the price of limiting enhancement resulting in the observed recalcitrance of crops such as soybeans to be bred or engineered for elevated protein content. The invention relates to molecular mechanisms that lead to a protein trait in seeds. The process of development and accumulation of seed reserves (protein, oil, starch) involves complex interacting mechanisms that activate and regulate large suites of genes as a regulon.

Some embodiments of the invention relate to key regulons such as the hormone abscisic acid that controls a vast array of seed genes by a seed-specific transcription factor that binds to ABF (abscisic acid factor) sequences upstream of the regulated gene. This can provide an on switch for the genes. To switch off the ABA-induced transcription the ABF transcription factor can be removed from the gene and degraded by an ubiquitin-mediated mechanism. Some embodiments of the invention relate to the E3-RING ubiquitin ligase protein that mediates the ABF degradation, or gene off.

In some embodiments, when a targeted protein is down-regulated by RNAi silencing or over-expressed using a sense construct containing the open reading frame regulated by the oleosin promoter and terminator—the resulting seeds can accumulate significantly more protein (as much as 8%+) with a higher Cysteine and Methionine content. With this approach, enhanced value soybean seeds with higher proportional seed protein content can be created.

Some embodiments of the invention relate to a polynucleotide including an active sequence capable of causing altered ABA-regulated gene expression in a plant and further including at least one other sequence capable of enabling or enhancing expression of the active sequence. In some embodiments, the active sequence comprises SEQ ID NOs 1 or 2. In some embodiments, the polynucleotide comprises an expression cassette including the active sequence, wherein the active sequence is linked to a promoter. In some embodiments, the promoter is oleosin. The promoter can also be other seed-specific promoters of soybean genes including glycinin and conglycinin storage proteins, lectins, kunitz trypsin inhibitor and potentially any other heterologous promoters including homologues of these proteins derived from other plant species.

Genetic elements of this invention can include soybean in origin including the primary transgene as well as the controlling upstream and downstream elements. As a result, except for vector materials, the experimental vector can be cis genetic with respect to soybean. Further, the construct design can be a CRISPR approach to achieve the same ends with targeted mutation that silences genes that can transcend some regulatory requirements.

Aspects of the invention can relate to increased protein and amino acid content in soybeans using constructs. Both protein and sulfur amino acids can be increased by about 8-10% as compared with controls. Gene expression levels in two lines (200X and 150X) over controls can be achieved. In a line, non-targeted metabolomics can be assayed and show a general increase in free amino acid flux that is necessary to support additional protein. The underlying biology can be a technology for engineering increased protein.

Prior decades of breeding experience have shown that protein content is a genotype—a line-specific, genetically determined trait that can be bred. Breeding lines with elevated protein content have exhibited lower yield that is not necessarily compensated by the value of increased protein content. The genes and pathways that confer elevated protein content in breeding lines has not been elucidated, so it is difficult to estimate how yield and protein content are mutually regulated. Engineering soybeans provides a different perspective to the issues of increasing protein content. Through engineering, specific known genes can be altered that can impact metabolic and/or regulated pathways as defined goals. With traits conferred by defined genetic modification the downstream analysis can specifically assess the impact on the seed's biological processes. Protein composition has input plasticity within the individual protein-content genotype resulting in environmental variability. For example, sulfur availability can modulate the mix of seed proteins while maintaining the genotype's protein content. Protein composition can also be varied by mutation or genetic engineering suppressing accumulation of major and minor seed proteins. Both mutation/selection and engineering are key tools to create improved soybean lines. From a biological perspective there are significant differences in the potential of mutation and selection compared to engineering. Mutant lines and variations have the genetic alteration in every cell of plant so that the mutation is always present. In contrast engineering can be conditional with the genetic change functioning for instance in only maturing seeds as outlined in this project. The overt limits of yield seen in breeding lines can result from the fact that the genetic change is systemically present and such limits can be circumvented by an engineering strategy.

Some embodiments of the invention relate to the AiP2 gene or the like. AiP2 regulation of steady-state amino acid abundance can have broad implications beyond engineering high-protein content seeds. The E3-ring ubiquitin ligases including AiP2 are among the most abundant genes in diverse eukaryotes including plants and humans. As a superabundant gene family many different functions have been assigned to individual gene members. In plants the activity of E3-ring ligase proteins mediates the degradation of the AiB3 transcription factor inducing ABA-regulated gene expression. ABA is intricately involved in the response to abiotic stress mediating the cascade of events that plants employ to mitigate the adverse environmental conditions. The function of E3-ring ubiquitin ligases in abiotic stress has shown that altering its expression can increase the sensitivity to stress amplifying on the important role of ABA-regulated gene expression in stress response. Nitrogen availability (N-availability) has an important role in stress response enabling massive turnover of existing cellular constituents and its replacement with new cellular components that either mitigate the stress or replace damaged components. Altered expression of other E3-Ring ubiquitin ligases has been shown to impact mitigation of abiotic stress. From a broader perspective among Eukaryotes and particularly in humans where E3 ring ubiquitin ligases are the most abundant gene type in the genome, the function of this gene has been correlated with a number of health-related disorders including cancer, controlling nutrient input to the tumor is central to devising treatment protocols. These results showing that a seed E3-ring ubiquitin ligase impacts the steady state amino acid flux and protein content has significance in the broader context of these other processes that are linked to N-availability.

Embodiments of the invention can relate to OE and RNAi silencing of the E3 ring ubiquitin ligase AiP2 in soybean seeds which result in similar global changes of the soybean seed composition indicating that it is the perturbation of the standard expression level of the AiP2 that induces altered composition. From the biological perspective the shortage of AiP2 protein could have a similar effect to its over-abundance as an interactive component of a regulatory system cascade. One possible explanation is found in the smaller silencing seeds and its larger proportional oil decrease that may result in a higher protein content because the seeds are slightly smaller and with less oil. The ABA regulon in seeds is diverse including the storage of proteins and enabling physiological systems that control seed development and maturation. The roles of ABA and the regulon controlled by ABA are well studied in many model and crop seed systems, but prior to the instant invention, altering ABA-regulated control processes in seeds has not been used as a biotechnology engineering strategy to improve composition, compared to the more numerous examples in abiotic stress, where ABA is central to the cascade of events to mitigate damage.

Proteome rebalancing can limit the capacity to breed or engineer altered seed protein content. In soybean where the production trend has been for less seed protein content, the biology of proteome rebalancing impedes improving seed protein. Embodiments of the invention can relate to altering the expression of this E3 ring ubiquitin to engineer seeds with increased protein that can meet stakeholder content goals for enhanced food and feed output traits.

Some embodiments of the invention relate to altering β-carotene. For example, genetic methods to improve β-carotene content in a plant can be combined with any aspect of the invention.

The invention relates to high-protein-content soybeans and methods of producing high-protein-content soybeans. The methods can relate to proteome rebalancing and regulating the abscisic acid (ABA) pathway. The methods can relate to modulating transcription factors such as AiP2. AiP2 modification can be an enabling technology to increase soybean protein content and indicates that the strategic path to alter seed protein is contained within the mechanisms of abscisic acid control of seed development.

EXAMPLES

Example 1

Protein Content and Protein Composition are Independently Regulated

The invention relates to a novel concept that separates the output traits of protein content and protein composition in a process termed proteome rebalancing. In a series of studies (Kinney et al 2001; Schmidt et al 2011; Herman 2014) the concept of proteome rebalancing was pioneered in which it was demonstrated that suppressing as much as 66% of the soybean storage protein accumulation still resulted in seeds that accumulate the standard protein content determined by genotype but over-producing other soybean seed proteins to replace the shortfall of storage proteins. With the knowledge that the soybean protein content genotype is so highly regulated that it will even compensate for a shortfall of a majority of the standard protein synthesis, an experimental model to determine how the protein content genotype is enforced can be set up. It can be determined how genetic regulating elements—transcription factors—that are altered in storage protein-suppressed (SP−) lines influence the manifestation of the seed protein content genotype.

Example 2

High B-Carotene Soybeans Indicate that the Path to Enhanced Protein Content Could Result From Engineering Abscisic Acid (ABA) Related Control Processes Experiments were conducted to show that directed engineering can yield a high-protein seed trait. The β-carotene content of soybean can be enhanced much in the same way β-carotene has been increased in Golden Rice. β-carotene trait results were striking with the soybeans acquiring a carrot color and containing 40 fold more carotene than the best Golden Rice and at present the current record of biofortification of crop. Calculations were that 23 soybean seeds would meet an adult RDA or Vitamin A. The β-carotene soybeans exhibited two collateral traits, enhanced protein content of 4-5% and a shift in fatty acid to mid-oleic of about 45%. The metabolic pathways of amino acids leading to proteins have little commonality with the pathway leading to β-carotene, so the engineered higher protein trait derives from processes unrelated to β-carotene accumulation. β-carotene levels can affect the level of the ABA which is one of the primary regulators of seed development (Schmidt et al 2015). Manipulating ABA-related processes can be used as an engineering strategy to produce increased seed protein.

Example 3

Engineering the ABA Regulation of Gene Activity Increases Protein Content

ABA is a primary regulator of seed development and storage substance accumulation. ABA regulates by a cascade of events in which the primary ABA molecule is recognized by a receptor that in turn transduces the signal to another protein that in turn activates a transcription factor that binds to a specific ABA-signal box in the upstream region of regulated genes. Within the seed there are hundreds of genes that have a ABA-regulation element that are each regulated by the ABA signal that together comprise an ABA regulated gene set or regulon. All of the storage proteins and ancillary seed proteins are members of the ABA regulon. For each ABA molecule signal one gene is activated, so to activate the entire regulon of hundreds of genes requires the signaling of a large number of ABA molecules. Once activated or "on," an ABA-activated gene does not simply remain on but rather each of these genes is dynamically deactivated or switched "off" by the removal and degradation of the ABA transcription factor. How long each member of the ABA regulon is either on or off functions in a combinatorial manner that as a sum yields protein content and composition. Although the two major storage proteins comprise 66% of the total seed protein, soybean seeds minus storage proteins still have the same protein content albeit with a vastly different protein composition, because other proteins are accumulated to compensate for the storage protein shortfall. Among the regulatory seed proteins that impacted storage protein silencing is AiP2, which mediates the deactivation of ABA-induced gene expression by tagging the ABA transcription factor for degradation.

Example 4

AIP2 Modified Seeds Exhibit a High Protein Trait

Figure 3:
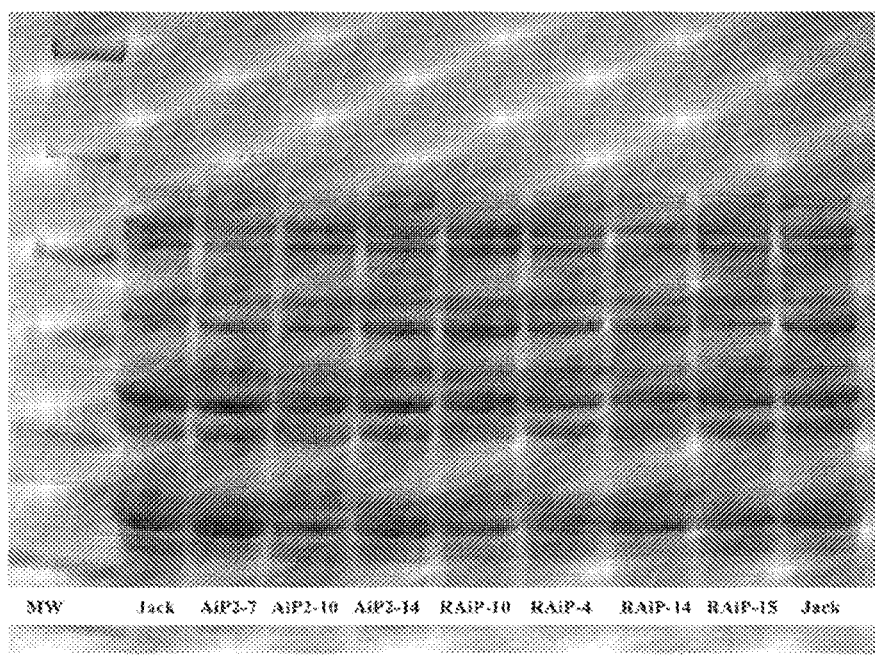
FIG. 3 depicts a SDS/PAGE gel showing the distribution of the major soybean seed proteins in various lines over-expressing and suppressing AIP2 compared to controls. The results of this experiment indicate that the change in protein content in the transgenic seeds encompasses a relatively global change in the major proteins rather than a specific increase or decrease of one or few proteins. Altering AiP2 expression shown in FIG. 2 does not result in large scales changes in the distribution of the types of proteins accumulated in the soybean seeds.

Soybean AiP2 expression was altered in soybean seeds by over-expressing the gene and by silencing intrinsic AiP2 expression by RNAi. Gene constructs were produced comprising the elements derived from the soybean oil body protein oleosin's promoter and terminator that was used to bracket either the ORF of the AiP2 protein (GenBank #XM_003550182.3) or an RNAi suppression sequence derived the E3-ring ubiquitin ligase identified from a differential transcriptome analysis of SP– and the parental cv Jack. To construct the modifying transgene the soybean oil body oleosin promoter was used for both the upstream and downstream regulatory elements (Rowley et al 1997). The selection of oleosin control was based on the observation that in proteome rebalancing, the fact that protein composition is altered but protein and oil content remain constant indicates that oleosin expression should be relatively independent of the proteome rebalancing mechanisms. This is important because analyzing potential changes in regulation is less complicated if the changes induced do not form a feedback loop with storage protein content. The use of the oleosin promoter is novel: all of the commercial literature, and (except for a single paper from the inventor's laboratory) every published soybean seed transgenic has used a seed vacuolar promoter, including promoters for the major storage proteins, lectin, and Kunitz trypsin inhibitor—promoters that may have a higher risk of a feedback loop with the protein accumulation processes being modified. After biolistic transfer of the transgene to soybean somatic embryos the recombinant plants were selected and regenerated to T0 plants and then seeds. Germinated T0 seeds' primary leaves were assessed for the presence of the transgene and grown to T1 generation that was repeated through the T2 and T3 generations. Homozygosity of T2 and T3 plants was assessed by real-time PCR of leaf genomic DNA. The altered expression pattern of the AiP2, E3 Ring ubiquitin ligase was analyzed using real time PCR of cDNA derived from mid-maturation seed mRNA. Compared to parental cv Jack the AiP2 7 and 14 overexpression lines displayed 150-300—fold increase in transcript abundance and the RNAi line 14 and 15 C displayed a decrease in transcript abundance (FIG. 3). A grow-out of homozygous T3 plants and seeds was used to assay the impact of altered AiP2 expression on the seed's overt seed traits and more detailed analysis of amino acid and fatty acid content, transcriptome, metabolome and proteome. Soybeans maintain a standard 2:1 ratio of protein:oil accumulation exemplified by parental line's cv Jack 1.93:1 protein:oil ratio. Perturbation of E3 Ring ubiquitin ligase expression by both over-expression and suppression increased total protein accumulation at the expense of oil altering the protein:oil to 2.5:1. The OE lines exhibited increased protein of 42-43% protein and 17% oil compared to about 36% protein and 18.5% oil of the parental cv Jack (Table 1). The dry weight of the AiP2 OE lines seeds averaged 15% larger than the parental while the AiP2 RNAi lines averaged 10% smaller with both the OE and RNAi seeds having similar overt morphology to the parental cv Jack seeds. The significance of the induced compositional change is the resulting seeds possess the protein+oil index of the AiP2 OE seeds is about 60%, just short of an ideal goal of 62% cited by Hurburgh et al (1990) for a stakeholder seed protein goal.

TABLE 1

| Line | Protein % | Cys/Met | Oil | P:O Ratio |
| --- | --- | --- | --- | --- |
| Jack | 35.74 | .62/.61 | 18.47 | 1:1.93 |
| AiP2-7 | 43.16 | .70/.70 | 16.68 | 1:2.59 |
| AiP2-14 | 42.73 | .78/.72 | 17.09 | 1:2.50 |
| AiP2R-14 | 39.80 | .73/.71 | 15.33 | 1:2.59 |
| AiP2R-15 | 41.46 | .83/.59 | 16.06 | 1:2.58 |

An analysis of the oil composition of seeds of both the AiP2 OE and RNAi lines showed an overall decrease of 18:1 (Oleic) FA from 27% to about 15% in favor of increased 18:2 and 18.3. In contrast, there was little variation of 16:0 in in both OE and RNAi lines compared to the parental cv Jack (Table 2). SDS/PAGE comparison of polypeptide distribution of the AiP2 OE and RNAi in comparison with the parental cv Jack showed little if any overt differences in the types and distribution of storage and ancillary seed proteins (FIG. 3). The total amino acid distribution assayed from seed protein hydrolysates showed an overall increase in abundance of amino acids proportional to the increase in protein content of the AiP2 modified seeds (FIG. 3). The increase in total protein and amino acid content appears to be enabled by changes in the metabolite profile of the developing seeds. The polypeptide patterns of the AiP2 OE and RNAi seeds were comparable to the cv Jack and did not exhibit significant differential abundance of the major seed proteins. This was further substantiated using non-targeted proteomics that also showed the increase in protein content resulting from altered AiP2 expression did not result from contributions of any specific seed protein. Soybeans are among the eight primary foods regulated by the Food Allergen Labeling Protection Act that in the USA requires soybean protein inclusion labeling in food to be identified due to food allergy risk. Soybean food allergens have been identified and characterized, for the AiP2 OE and RNAi seeds the non-targeted proteomics did not identify any soybean allergen that is differentially increased over the parental line. These results indicate that engineering strategies can be designed to increase soybean protein content in excess of stakeholder goals without differentially increasing food safety issues resulting from allergens.

TABLE 2

| | wt. | | | | | | AVG ug/mg | | | | | | |
| --- | --- | --- | --- | --- | --- | --- | --- | --- | --- | --- | --- | --- | --- |
| Line# | (mg) | Total | 16:0 | 16:1 | 18:0 | 18:1 | 18:2 | 18:3 | 20:0 | 20:1 | 22:0 | 22:1 | 24:0 |
| Control | 13.27 | 198.8 | 22.1 | 0.2 | 6.0 | 33.3 | 120.9 | 14.7 | 0.4 | 0.3 | 0.5 | 0.1 | 0.2 |
| Jack | 16.04 | 208.4 | 21.7 | 0.2 | 5.8 | 57.4 | 109.9 | 11.6 | 0.5 | 0.4 | 0.6 | 0.0 | 0.3 |
| AiP2-7 | 12.77 | 165.9 | 17.9 | 0.1 | 5.8 | 23.3 | 102.6 | 14.5 | 0.5 | 0.3 | 0.7 | 0.0 | 0.3 |

TABLE 2-continued

| | | | | | | AVG | | | | | | |
|---|---|---|---|---|---|---|---|---|---|---|---|---|
| AiP2-14 | 15.72 | 190.8 | 21.6 | 0.2 | 5.8 | 34.3 | 112.3 | 15.0 | 0.5 | 0.3 | 0.5 | 0.0 | 0.3 |
| RAiP-14 | 14.56 | 172.5 | 18.7 | 0.1 | 5.6 | 23.9 | 108.0 | 14.7 | 0.5 | 0.3 | 0.5 | 0.0 | 0.3 |
| RAiP-15 | 11.20 | 178.5 | 20.4 | 0.2 | 5.6 | 27.8 | 107.9 | 14.8 | 0.6 | 0.3 | 0.6 | 0.0 | 0.3 |

| | wt. | | | | | | % | | | | | | |
|---|---|---|---|---|---|---|---|---|---|---|---|---|---|
| Line# | (mg) | Oil | 16:0 | 16:1 | 18:0 | 18:1 | 18:2 | 18:3 | 20:0 | 20:1 | 22:0 | 22:1 | 24:0 |
| Control | 12.22 | 19.9 | 11.1 | 0.1 | 3.0 | 16.7 | 60.8 | 7.4 | 0.2 | 0.2 | 0.3 | 0.1 | 0.1 |
| Jack | 16.04 | 20.8 | 10.4 | 0.1 | 2.8 | 27.5 | 52.7 | 5.6 | 0.2 | 0.2 | 0.3 | 0.0 | 0.1 |
| AiP2-7 | 12.48 | 16.6 | 10.8 | 0.1 | 3.5 | 14.0 | 61.8 | 8.7 | 0.3 | 0.2 | 0.4 | 0.0 | 0.2 |
| AiP2-14 | 13.06 | 19.1 | 11.3 | 0.1 | 3.0 | 18.0 | 58.8 | 7.9 | 0.2 | 0.2 | 0.3 | 0.0 | 0.2 |
| RAiP-14 | 11.20 | 17.2 | 10.8 | 0.1 | 3.2 | 13.8 | 62.6 | 8.5 | 0.3 | 0.1 | 0.3 | 0.0 | 0.2 |
| RAiP-15 | 12.19 | 17.9 | 11.4 | 0.1 | 3.1 | 15.5 | 60.5 | 8.3 | 0.3 | 0.2 | 0.4 | 0.0 | 0.2 |

Figure 5:
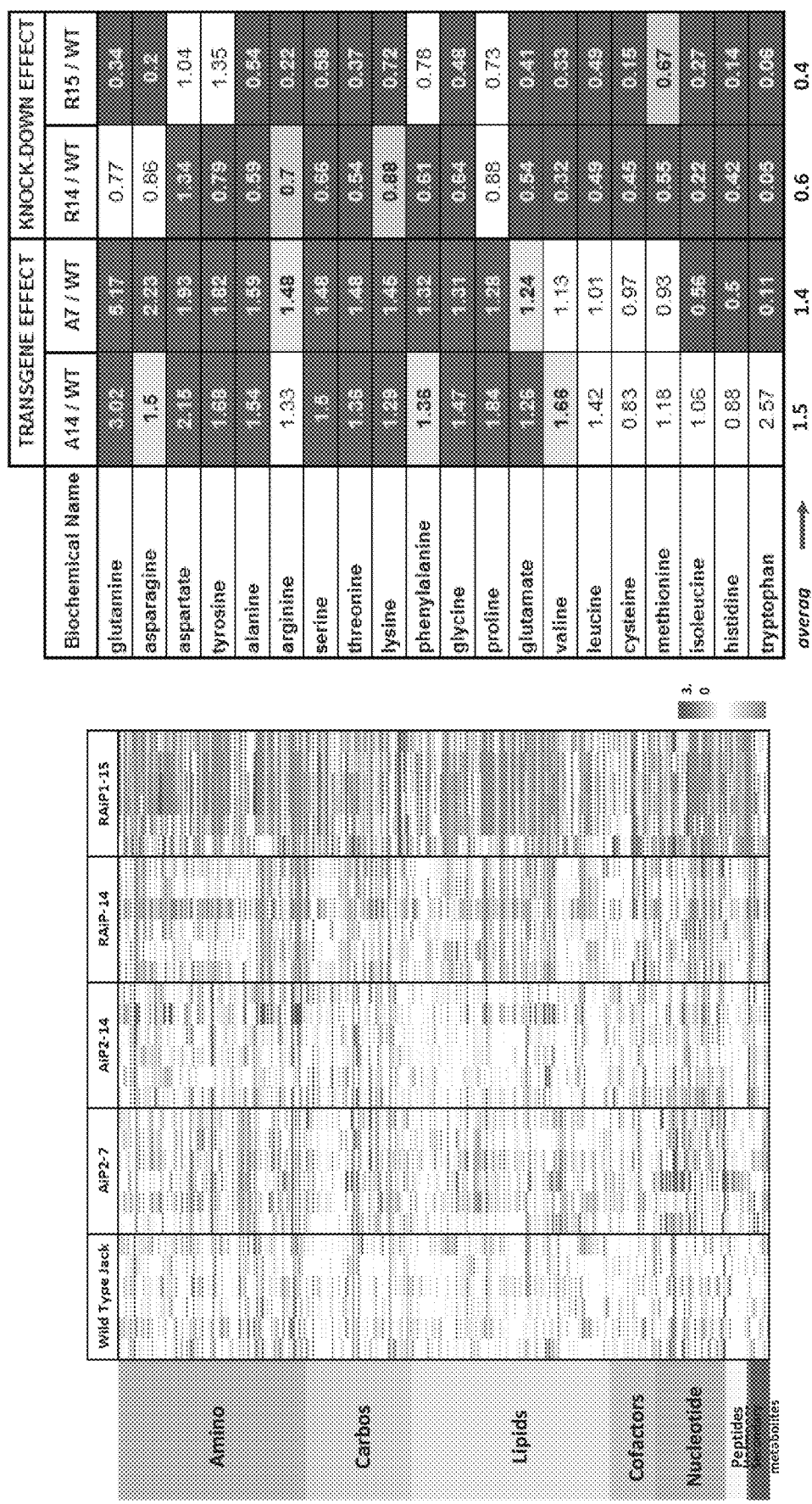
FIG. 5 depicts the change in metabolite content in control and seeds expressing and suppressing AiP2. AiP2 over-expression resulted in enhanced free amino acid abundance comprising a majority of the amino acid types. In comparison the RNAi silencing of AiP2 transcripts resulted in a modest decrease in free amino acids. This result shows that AiP2 over-expression enables a nitrogen-push supplying additional nutrient flux enabling altering seed content.

To assess whether changes in nutrient availability enables the high-protein trait, mid-maturation seed cotyledons were surveyed for alterations of metabolite profile. Non-targeted metabolomic profile of 350 diverse metabolites showed that the primary differences between the seeds with altered AiP2 expression was in the abundance of amino acids and a few other nitrogenous molecules (FIG. 5). The AiP2 OE lines manifest significant increase in free amino acid abundance while the RNAi lines exhibit the inverse effect of a decrease in free amino acids. Unlike the SP-seeds that differentially exhibited a selective increase in free Asn, the amino acid changes in the AiP2 seeds comprised several different types of amino acids including Asn and Gln N-source metabolites.

Figure 4:
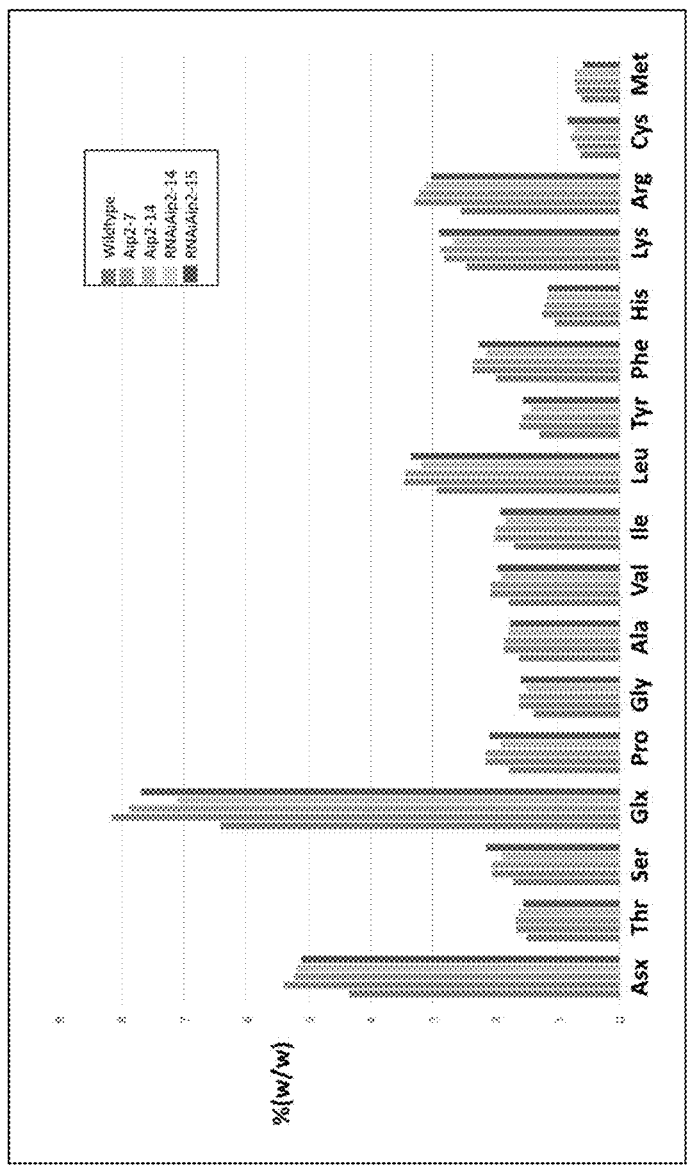
FIG. 4 depicts the comparison of the total amino acid of the AiP2 over-expressing and silencing lines with control cv Jack. AiP2 modification results in an increase in total amino acid composition proportional to the increase in protein content.

The analysis of the AiP2 lines showed that both the over-expression and silencing of the gene results in additional protein accumulation. Proteomic and protein gel analysis indicated that the protein increases were relatively global not favoring any specific types of proteins. Total amino acid content of the AiP2 lines showed greater seed amino content with the sulfur amino acid increased proportional to the protein increase (FIG. 4). Amino acid metabolite of one of the lines (AiP2-7) showed that the increase in protein may be enabled by increases in free amino acid flux (FIG. 4). This indicated that the alteration of AiP2 can change the amino acid flux in soybean enabling an increase in protein accumulation. Over-expressing AiP2 in soybean resulted in a substantial increase in source amino acids that enables increasing protein.

Example 5

Engineering of High Protein Seeds

Soybean seeds engineered to accumulate elevated protein content can be produced and tested. The utility for this trait can be assessed in a test field environment to evaluate yield. Use of two engineering strategies that yield higher level of seed protein content can be additive. An artificial storage protein gene that encodes a protein reporter can be used to test how the inventive methods can yield increased protein. New biotechnology traits introduced into soybean can share increased protein accumulation.

Example 6

High Protein AiP2 Soybean Lines

The engineering of the AiP2 resulted in elevated protein in greenhouse grown plants. Field tests related to quality of the trait and its possible effect on yield can be conducted. Although high-protein breeding lines often, if not always, exhibit yield drag that may mitigate the additional value of a high-protein trait, parallel tests have not been conducted on engineered high protein lines. Field tests can examine whether this strategy to increase protein alters yield or whether engineering dominant transgene traits circumvents the yield issues observed in breeding lines.

The AiP2 over-expression and RNAi soybean lines were characterized. Assays completed included transcriptome and proteome comparisons with the parental cv Jack line. Metabolomic assessment of one line AiP2-7 showed a general increase in amino acid flux compared to the control cv Jack that is consistent with global protein increase. Other lines can be characterized for metabolome and flux to ascertain whether this is a general characteristic of increasing protein content. Spot checks of gene expression using real-time PCR assays can confirm the results of global proteome and transcriptome assays. The real-time PCR can encompass about 20 select genes for each of the experimental lines and control. Completing the assessments of the underlying biology of AiP2 transgenics can provide useful information for use of the invention.

Example 7

Greenhouse Test of High Protein AiP2 Soybean Lines

To evaluate the lines in hand a statistically valid set of plants can be grown in parallel to controls to produce sufficient seed to evaluate performance of the high protein trait. The seeds produced can be assessed for protein content and composition, amino acid content, weight, oil content, and production in comparison with control.

Example 8

Field Test of High Protein AiP2 Soybean Lines

To field evaluate the high protein seeds several hundred plants for each line for example can be grown with controls at a facility meeting USDA/APHIS requirements. The seed harvested from the field test can be assessed for protein content and composition, amino acid content, weight, oil content, and production in comparison with control. The field test can evaluate if the greenhouse observation of high protein and increased sulfur amino acid content is produced under agronomic circumstances. The field test can identify any issues of yield drag in comparison with controls as has been observed in breeding high-protein lines.

Example 9

Creating a High-Protein, Low Protein Bioactivity Soybean

To further enhance value of high protein lines, the protein composition can be altered to be more favorable for end uses such as feed or protein processing. This approach can be deployed in oil to improve composition and to increase value with enhanced oleic acid content. For seed protein, the comparative changes needed include reduction in soybean's bioactivity both in metabolic inhibitors and allergens. A conventional breeding line, Triple Null, which lacks Kunitz Trypsin inhibitor, lectin, and the dominant P34 allergen has been created (Schmidt et al. 2015). The Triple Null line is transformable (Schmidt and Herman, 2016) using standard protocols. To test the capacity to increase the protein content of Triple Null this line can be transformed with the same construct previously used in cv Jack. The resulting transformants can be selected and regenerated into plants, selected for three generations to produce homozygous plants and evaluated for trait.

Standard Triple null is a performance test. Atlantic salmon have been shown to be soybean meal intolerant with resulting reduced growth rates in substitution for fish meal that appears to be in large part due to Kunitz Trypsin Inhibitor and Lectin (see Schmidt and Herman 2016 for review). Triple Null lacks these two proteins and is used to test whether this soybean line's suitability as a soybean protein substitution for fishmeal. Soybean as an aquaculture feed is renewable, scalable, and available at a fraction of the cost of fishmeal. Soybean meal has a lower protein and sulfur amino acid content than fishmeal that can be addressed by engineering a high protein/increased sulfur amino acid content version of Triple Null. The AiP2 gene can be transferred to Triple Null to provide a direct path to exploit Triple Null as an engineering platform for enhanced feed producing a low bioactivity high protein soybean, essentially a "better bean" using alleles and genetic elements all derived from soybean.

Triple Null was demonstrated to be transformable by biolistic transformation (see Schmidt and Herman, 2016). To create a high protein Triple Null line the same AiP2 construct used in cv Jack can be used to create a minimum of 5 independent insertion events. The resulting transformants can be regenerated into plants to produce T0 generation seeds that will be re-selected over 2-3 more generations to produce homozygous AIP2/Triple Null lines. The resulting homozygous seeds can be assessed for protein content and composition as well as general seed characteristics of size, weight, oil, and carbohydrate content. If AiP2 produces a parallel high-protein trait as previously shown in AiP2/Jack seeds this can create seeds that can yield high-protein low bioactivity soybean meal useful as aquaculture and other feed use.

The process to produce the T0 generation of transgenic soybeans requires about 9 months total from the initial transformation, selection of plants, regeneration, and growth to the first T0 seed. Then the seeds can be evaluated for over composition and content. A further two or more generations of about 120 days each are needed to produce homozygous seeds. Homozygous status can be confirmed by real-time PCR and the overt trait analyzed in year 2 with larger expansion/analysis of material in year 3.

Example 10

Additive Alleles for Increased Protein Content

Since β-carotene and AIP2 variations both yield high-protein traits, there can be an additive effect by co-expressing both transgenes to regulate additional protein content by altering ABA and for AiP2 to regulate additional protein by impeding the deactivation of ABA-regulated genes. The high protein β-carotene trait can be stacked with the high protein AiP2 trait and the resulting protein content output trait can be assessed. Stacking two separate high protein traits can be additive in driving the protein content of soybean seeds to higher levels.

Homozygous cv Jack b-carotene lines and AiP2 lines are available. Using β-carotene lines as the pollen donor can create dominant orange color in successful crosses resulting in merged lines for the two transgene traits. A minimum of five independent crosses can be obtained with the over expression and RNAi AiP2 lines with the β-carotene line. The resulting seeds can be reselected to obtain homozygous seeds stacking both transgenes. The resulting seeds can be assessed for protein, oil, size, weight, composition, and protein composition together with fatty acid profile for oleic acid status as well as ABA content. These assays can critically test whether stacking two high-protein transgenic types is additive yielding still higher protein content that will provide further enabling approaches to produce enhanced soybean seed protein content. Other types of metabolic engineering that could increase seed ABA content without producing collateral β-carotene can be designed. Using the present β-carotene line enables a conceptual test of stacking high protein traits without the necessity to produce new transgenics, a lengthy process. (Schmidt and Herman 2008).

Example 11

Greenhouse Test of B-Carotene/AiP2 Cross Products

To evaluate the lines, a statistically valid set of plants can be grown in parallel to controls to produce sufficient seed to evaluate performance of the high protein trait. The seeds produced can be assessed for protein content and composition, amino acid content, weight, oil content, and production in comparison with control. The greenhouse test can expand seed to undertake a field performance test. The donor parent lines (AiP2 and β-carotene) can be grown in parallel as control composition seeds to assess whether stacking the high protein is additive. A full suite of assays can evaluate the β-carotene/AiP2 cross products. These assays can parallel those previously accomplished in developing the β-carotene and AiP2 traits including seed composition, seed transcriptome, proteome, and metabolome that together can assess the collateral alteration in seed biology that occurs in producing a stacked high protein trait.

Example 12

Field Test of B-Carotene/AiP2 Cross Products

To field evaluate the high protein seeds, several hundred plants for each line can be grown with controls at a facility meeting USDA/APHIS requirements. The seed harvested from the field test can be assessed for protein content and composition, amino acid content, weight, oil content, and production in comparison with control. The field test can evaluate if the greenhouse observation of high protein and increased sulfur amino acid content is produced under agronomic circumstances. The field test can identify any issues of yield drag in comparison with controls as has been observed in breeding high-protein lines.

Example 13

Biotechnology Traits

ABA related regulation through potentially greater ABA flux derived from enhancing β-carotene or by impeding the deactivation of ABA-induced genes by AiP2 functions through the ABA-gene regulatory elements common to soybean storage proteins and other ancillary seed proteins. Most of the gene regulatory elements used by industrial and academic soybean biotechnologists are storage protein elements that contain the ABA regulatory element. Biotechnology traits can participate in enhanced protein content. Exploiting AiP2 can enhance protein content. Schmidt and Herman (2008) have shown that the fluorescent protein GFP can be used as a reporter for the gene expression and protein accumulation of the major storage protein glycinin. By using the gene expression controlling domains of glycinin and exchanging the GFP for the glycinin coding sequence creates a GFP that is controlled and regulated like glycinin and more broadly a proxy for an introduced biotechnology traits. Because glycinin accumulation increases in AiP2 seeds then it follows that a glycinin proxy as a glycinin regulatory element controlled GFP should also increase in the AiP2 background. This approach can test whether a biotechnology trait is enhanced by AiP2 and demonstrate that it is modulated by ABA. To accomplish this goal, the GFP soybean as pollen donor can be crossed with the AIP2 soybeans with successful crosses being fluorescent as shown. The resulting crosses can be regrown for two generations to identify homozygous plants for both traits. GFP/AiP2 seeds can accumulate a greater level of GFP than the GFP parent that is assayed by fluorometry. To test for variations in accumulation by ABA, control GFP soybeans and GFP/AiP2 immature seeds can be used to generate somatic embryos. To test ABA control of GFP accumulation and more specifically enhanced accumulation of GFP in the AiP2 crosses the ABA level can be varied in the tissue culture media. The reason for using tissue culture somatic embryos for this experiment rather than seeds is that it is difficult, if at all possible, to vary ABA in intact pods/seeds. In contrast, the culture of somatic embryos enables bath exposure to varying level of ABA ensuring more accurate assays. Somatic embryo cultures of this type have been used to study nutrition requirements for seed development, therefore there is a large body of literature supporting this technical approach.

The GFP and AiP2 can be crossed using the GFP as a pollen donor. Successful crosses can be propagated and reselected. The initial cross and at least one generation of selection will occur in year one. Reselection of GFP/AiP2 can continue until homozygous plants are obtained these will be regrown to obtain immature seeds to induce somatic embryos. At the end of year 2 or into year 3 the tests on the AiP2/GFP somatic embryos can be accomplished. The somatic embryos can be cultured in the presence of varying levels of ABA and the output traits of GFP accumulation as a proxy for glycinin and other biotechnology products documented. The assays can include GFP accumulation, somatic embryo protein accumulation pattern, total and free amino acids, and over growth measurements.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the invention disclosed herein are illustrative of the principles of the embodiments of the invention. Other modifications that can be employed can be within the scope of the invention. Thus, by way of example, but not of limitation, alternative configurations of the embodiments of the invention can be utilized in accordance with the teachings herein. Accordingly, embodiments of the present invention are not limited to that precisely as shown and described.

Sequences:
SEQ ID No. 1:
PREDICTED: Glycine max E3 ubiquitin-protein ligase AIP2-like (LOC100800189), mRNA

```
NCBI Reference Sequence: XM_003550182.3
    1 atatacatca aaacacgcag aagaagaaga accttacaaa gggcttttga attttcgtgt
   61 tttgatcaga atcagaggaa aaaatcacat aatttcgaat tcaaaatttg aattttcgtg
  121 tataaaacga agagaagaga atggaatcgg aggatttggt gaagcaggaa ttggaggaat
  181 tgcagaaaca attggggaag aagctaaaat ttgaagcctc tatttcgtct ctaaaatctc
  241 ttctccaacg cacttaccca tcagcttccc cagcgcttcg caaatccttt tatttggtta
  301 tatgccgagt tgctactgtg ttgaagacca ggtatacagc accaggtttc tggaatgctg
  361 gactgggcct ttttgagcag gctcatttgc ttgtttctga accttctgag aaggagaagt
  421 tgaaggcttg cattgctcag gccagggaac atttgcatct agaagataac ccatcacaag
  481 ctttacaacc ttcagataat caggcaaaca gaggatatct ttttgagggg caccttacgg
  541 ttgatcctga gccaccacag cctcaatggt tggtgcagtc aaacctcttg acaacagctg
  601 ctacactctt tgctgctgaa tcctctcaag ctccagcagc aaatgaaacc actcaagagg
  661 atgccgcaaa tatgcttcaa gatcttctaa atagattgga agaagttgtg cccttgatgg
  721 tggatggagg tcctgtagcc ccaaaagcac ctcctgccag taaagaggtt gtggcaaatc
  781 ttccggtcat tactctcaca gaggaaatcc tggctaattt ggggaaagat gcagagtgtg
  841 ctatttgcag ggagaacttg gttttaaatg acaaaatgca agagttgcca tgcaagcaca
  901 cattccaccc accatgtcta aagccatggc tggatgagca caattcttgt cccatctgtc
  961 ggcatgagct gcaaactgat gatcatgcct atgagagctg gaaggagcgt gaaaaggaag
 1021 ctgaagaaga gaggaaaggt gctgaaaatg caattcgagg tggtgaatac atgtatgttt
 1081 aaatgaccat tcaatgtatg gtttaataat atggttgttc gtgtaacaat ggatttgaaa
 1141 tcttcatctg gtgaatagtt gtgtattctt tattgtttca tgttatggag atatctcaaa
 1201 tttttaggga tg
```

SEQ ID No. 2
PREDICTED: E3 ubiquitin-protein ligase AIP2-like [Glycine max]
NCBI Reference Sequence: XP_003550230.1

```
  1 mesedlvkqeleelqkqlgk klkfeasiss lksllqrtyp saspalrksf ylvicrvatv
 61 lktrytapgf wnaglglfeq ahllvsepse keklkaciaq arehlhledn psqalqpsdn
121 qanrgylfeg hltvdpeppq pqwlvqsnll ttaatlfaae ssqapaanet tqedaanmlq
181 dllnrleevv plmvdggpva pkappaskev vanlpvitlt eeilanlgkd aecaicrenl
241 vindkmqelp ckhtfhppcl kpwldehnsc picrhelqtd dhayeswker ekeaeeerkg
301 aenairggey myv
```

REFERENCES

1. Kinney A J, Jung R and Herman E M (2001) Cosuppression of the α-subunits of β-conglycinin in transgenic soybean seeds induces the formation of endoplasmic reticulum-derived protein bodies. Plant Cell 13:1165-1178.
2. Schmidt M A, Barbazuk W B, Stanford M, May G, Song Z, Hong W, Nikolau B J, Herman E M (2011) Silencing of soybean seed storage proteins results in a rebalanced protein composition preserving seed protein content without major collateral changes in the metabolome and transcriptome. Plant Physiology 156: 330-345.

3. Herman, E M (2014) Soybean Seed Proteome Rebalancing. Front. Plant Sci. 5:437. doi: 10.3389/fpls.2014.00437.
4. Schmidt, M A, Parrott, W A, Hildebrand, D F, Berg, R H, Cooksey, A, Pendarvis, K, He, Y, McCarthy, F, and Herman, E M (2015) Transgenic soya bean seeds accumulating β-carotene exhibit the collateral enhancements of oleate and protein content traits. Plant Biotechnol. J. 13: 590-600. doi: 10.1111/pbi.12286.
5. Rowley D L and Herman E M (1997) The upstream domain of soybean oleosin genes contains regulatory elements similar to those of legume storage proteins. Biochim. Biophys. Acta. 1345:1-4.
6. Schmidt, M A and Herman, E M (2016) The potential of engineering functional-feed soybeans for sustainable aquaculture feed. Front Plant Sci. 2016; 7: 440. Doi: 10.3389/fpls.2016.00440.
7. Schmidt M A, and Herman E M (2008) Proteome rebalancing in soybean seeds can be exploited to enhance foreign protein accumulation. Plant Biotech J 6: 832-842.

What is claimed is:

1. A transgenic soybean plant transformed with a recombinant nucleic acid molecule comprising an RNAi expression cassette that targets endogenous Aip2 (ABI3-interacting protein 2) coding sequence as set forth in SEQ ID NO: 1 which encodes the endogenous Aip2 protein as set forth in SEQ ID NO: 2, wherein said RNAi expression cassette comprises a heterologous seed-specific promoter operably linked to a DNA sequence encoding an inhibitory RNAi molecule which corresponds to the nucleotide sequence of SEQ ID NO: 1 encoding the Aip2 protein of SEQ ID NO: 2, wherein overexpression of said inhibitory RNAi molecule decreases endogenous Aip2 protein of SEQ ID NO: 2 in transgenic seeds of said transgenic soybean plant, and thereby increases total seed protein content in said transgenic soybean plant seeds as compared to a control soybean plant seeds lacking said recombinant nucleic acid molecule.

2. A vector comprising a recombinant nucleic acid molecule comprising an RNAi expression cassette that targets endogenous Aip2 (ABI3-interacting protein 2) coding sequence as set forth in SEQ ID NO: 1 which encodes the endogenous Aip2 protein as set forth in SEQ ID NO: 2, wherein said RNAi expression cassette comprises a heterologous seed-specific promoter operably linked to a DNA sequence encoding an inhibitory RNAi molecule which corresponds to the nucleotide sequence of SEQ ID NO: 1 encoding the Aip2 protein of SEQ ID NO: 2, wherein overexpression of said inhibitory RNAi molecule decreases endogenous Aip2 protein of SEQ ID NO: 2 in soybean plant seeds transformed with said vector and thereby increases total seed protein content in said transformed soybean plant seeds as compared to a control soybean plant seeds lacking said recombinant nucleic acid molecule.

3. A method of obtaining a transgenic soybean plant seed with increase in total seed protein content comprising:
(i) transforming soybean plant cells with a recombinant nucleic acid molecule comprising an RNAi expression cassette that targets endogenous Aip2 (ABI3-interacting protein 2) coding sequence as set forth in SEQ ID NO: 1 which encodes the endogenous Aip2 protein as set forth in SEQ ID NO: 2, wherein said RNAi expression cassette comprises a heterologous seed-specific promoter operably linked to a DNA sequence encoding an inhibitory RNAi molecule which corresponds to the nucleotide sequence of SEQ ID NO: 1 encoding the Aip2 protein of SEQ ID NO: 2;
(ii) obtaining transgenic soybean plants from said transformed soybean plant cells of step (i); and
(iii) selecting a transgenic soybean plant from said transgenic soybean plants of step (ii) that overexpresses said inhibitory RNA molecule in transgenic soybean seeds of said selected transgenic soybean plant and exhibits increase in total seed protein content in said transgenic soybean plant seeds as compared to a control soybean plant seeds lacking said recombinant nucleic acid molecule.

4. The method of claim 3, further comprising harvesting transgenic soybean plant seeds from the selected transgenic soybean plant of step (iii).

* * * * *

SEQUENCE LISTING

```
<160> NUMBER OF SEQ ID NOS: 2

<210> SEQ ID NO 1
<211> LENGTH: 1212
<212> TYPE: DNA
<213> ORGANISM: Artificial Sequence
<220> FEATURE:
<223> OTHER INFORMATION: Glycine max

<400> SEQUENCE: 1
atatacatca aaacacgcag aagaagaaga accttacaaa gggcttttga attttcgtgt      60
tttgatcaga atcagaggaa aaaatcacat aatttcgaat tcaaaatttg aattttcgtg     120
tataaaacga agagaagaga atggaatcgg aggatttggt gaagcaggaa ttggaggaat     180
tgcagaaaca attggggaag aagctaaaat ttgaagcctc tatttcgtct ctaaaatctc     240
ttctccaacg cacttaccca tcagcttccc cagcgcttcg caaatccttt tatttggtta     300
tatgccgagt tgctactgtg ttgaagacca ggtatacagc accaggtttc tggaatgctg     360
gactgggcct ttttgagcag gctcatttgc ttgtttctga accttctgag aaggagaagt     420
tgaaggcttg cattgctcag gccagggaac atttgcatct agaagataac ccatcacaag     480
ctttacaacc ttcagataat caggcaaaca gaggatatct tttgaggg cacccttacgg      540 ttgatcctga gccaccacag cctcaatggt tggtgcagtc aaacctcttg acaacagctg     600
ctacactctt tgctgctgaa tcctctcaag ctccagcagc aaatgaaacc actcaagagg     660
atgccgcaaa tatgcttcaa gatcttctaa atagattgga agaagttgtg cccttgatgg     720
tggatggagg tcctgtagcc ccaaaagcac ctcctgccag taaagaggtt gtggcaaatc     780
ttccggtcat tactctcaca gaggaaatcc tggctaattt ggggaaagat gcagagtgtg     840
ctatttgcag ggagaacttg gttttaaatg acaaaatgca agagttgcca tgcaagcaca     900
cattccaccc accatgtcta aagccatggc tggatgagca caattcttgt cccatctgtc     960
ggcatgagct gcaaactgat gatcatgcct atgagagctg gaaggagcgt gaaaaggaag    1020
ctgaagaaga gaggaaaggt gctgaaaatg caattcgagg tggtgaatac atgtatgttt    1080
aaatgaccat tcaatgtatg gtttaataat atggttgttc gtgtaacaat ggatttgaaa    1140
tcttcatctg gtgaatagtt gtgtattctt tattgtttca tgttatggag atatctcaaa    1200
tttttaggga tg                                                       1212

<210> SEQ ID NO 2
<211> LENGTH: 313
<212> TYPE: PRT
<213> ORGANISM: Glycine max
```

-continued

```
<400> SEQUENCE: 2

Met Glu Ser Glu Asp Leu Val Lys Gln Glu Leu Glu Glu Leu Gln Lys
1               5                   10                  15

Gln Leu Gly Lys Lys Leu Lys Phe Glu Ala Ser Ile Ser Ser Leu Lys
                20                  25                  30

Ser Leu Leu Gln Arg Thr Tyr Pro Ser Ala Ser Pro Ala Leu Arg Lys
            35                  40                  45

Ser Phe Tyr Leu Val Ile Cys Arg Val Ala Thr Val Leu Lys Thr Arg
50                      55                  60

Tyr Thr Ala Pro Gly Phe Trp Asn Ala Gly Leu Gly Leu Phe Glu Gln
65                      70                  75                  80

Ala His Leu Leu Val Ser Glu Pro Ser Glu Lys Glu Lys Leu Lys Ala
                85                  90                  95

Cys Ile Ala Gln Ala Arg Glu His Leu His Leu Glu Asp Asn Pro Ser
            100                 105                 110

Gln Ala Leu Gln Pro Ser Asp Asn Gln Ala Asn Arg Gly Tyr Leu Phe
        115                 120                 125

Glu Gly His Leu Thr Val Asp Pro Glu Pro Pro Gln Pro Gln Trp Leu
    130                 135                 140

Val Gln Ser Asn Leu Leu Thr Thr Ala Ala Thr Leu Phe Ala Ala Glu
145                 150                 155                 160

Ser Ser Gln Ala Pro Ala Ala Asn Glu Thr Thr Gln Glu Asp Ala Ala
                165                 170                 175

Asn Met Leu Gln Asp Leu Leu Asn Arg Leu Glu Glu Val Val Pro Leu
            180                 185                 190

Met Val Asp Gly Gly Pro Val Ala Pro Lys Ala Pro Pro Ala Ser Lys
        195                 200                 205

Glu Val Val Ala Asn Leu Pro Val Ile Thr Leu Thr Glu Glu Ile Leu
    210                 215                 220

Ala Asn Leu Gly Lys Asp Ala Glu Cys Ala Ile Cys Arg Glu Asn Leu
225                 230                 235                 240

Val Leu Asn Asp Lys Met Gln Glu Leu Pro Cys Lys His Thr Phe His
                245                 250                 255

Pro Pro Cys Leu Lys Pro Trp Leu Asp Glu His Asn Ser Cys Pro Ile
            260                 265                 270

Cys Arg His Glu Leu Gln Thr Asp Asp His Ala Tyr Glu Ser Trp Lys
        275                 280                 285

Glu Arg Glu Lys Glu Ala Glu Glu Arg Lys Gly Ala Glu Asn Ala
    290                 295                 300

Ile Arg Gly Gly Glu Tyr Met Tyr Val
305                 310
```